United States Patent
Massey, Jr.

(10) Patent No.: US 9,533,101 B2
(45) Date of Patent: Jan. 3, 2017

(54) MULTI-CYCLE AND AUTO-DISABLE SYRINGE AND METHOD OF USE THEREOF

(71) Applicant: Leonard Allen Massey, Jr., Fort Valley, GA (US)

(72) Inventor: Leonard Allen Massey, Jr., Fort Valley, GA (US)

(*) Notice: Subject to any disclaimer, the term of this patent is extended or adjusted under 35 U.S.C. 154(b) by 770 days.

(21) Appl. No.: 13/828,559

(22) Filed: Mar. 14, 2013

(65) Prior Publication Data

US 2014/0276637 A1    Sep. 18, 2014

(51) Int. Cl.
*A61M 5/24* (2006.01)
*A61M 5/50* (2006.01)

(52) U.S. Cl.
CPC ............ *A61M 5/2448* (2013.01); *A61M 5/508* (2013.01)

(58) Field of Classification Search
CPC   A61M 5/508; A61M 5/2448; A61M 5/31511; A61M 5/50; A61M 2005/5093; A61M 2005/3123; A61B 5/150213; A61J 1/2096
USPC ............................... 604/518, 82, 110; 141/2
See application file for complete search history.

(56) References Cited

U.S. PATENT DOCUMENTS

| | | | |
|---|---|---|---|
| 4,248,246 A | 2/1981 | Ikeda | |
| 4,270,536 A | 6/1981 | Lemelson | |
| 4,299,238 A | 11/1981 | Baidwan et al. | |
| 4,424,817 A | 1/1984 | Williams | |
| 4,572,210 A | 2/1986 | McKinnon | |
| 4,632,672 A | 12/1986 | Kvitrud | |
| 4,690,154 A * | 9/1987 | Woodford | A61B 5/1405 600/578 |
| 4,728,321 A | 3/1988 | Chen | |
| 4,735,311 A | 4/1988 | Lowe et al. | |
| 4,801,295 A | 1/1989 | Spencer | |
| 4,816,021 A | 3/1989 | Johnson | |
| 4,874,372 A | 10/1989 | McArthur et al. | |
| 5,026,345 A | 6/1991 | Teringo | |
| 5,037,382 A | 8/1991 | Kvorning et al. | |
| 5,045,063 A | 9/1991 | Spielberg | |
| 5,084,027 A | 1/1992 | Bernard | |
| 5,238,003 A | 8/1993 | Baidwan et al. | |
| 5,246,011 A | 9/1993 | Caillouette | |
| 5,431,630 A | 7/1995 | Leonard | |
| 5,685,846 A * | 11/1997 | Michaels, Jr. | A61M 5/31596 604/181 |
| 5,865,803 A | 2/1999 | Major | |
| 7,063,683 B2 | 6/2006 | Teringo | |
| 7,635,344 B2 * | 12/2009 | Tennican | A61J 1/2096 604/82 |
| 2002/0198500 A1* | 12/2002 | Leung | A61M 5/508 604/231 |

OTHER PUBLICATIONS

International Search Authority, "International Search Report and Written Opinion," PCT/US14/21783, mailed Jun. 23, 2014.

* cited by examiner

*Primary Examiner* — Theodore Stigell
*Assistant Examiner* — Amber Stiles
(74) *Attorney, Agent, or Firm* — Meunier Carlin & Curfman LLC (57) ABSTRACT

A syringe device that includes a stem, container, and a plunger, the plunger having tubes with a soluble substance that maintain a seal on compounds within the container's chamber, and/or a parabolic cover held in position by a soluble substance, thus allowing a multi-cycle usage to dispense medication to patients, even while preventing further use.

26 Claims, 9 Drawing Sheets

MULTI-CYCLE AND AUTO-DISABLE
SYRINGE AND METHOD OF USE THEREOF

CROSS-REFERENCE TO RELATED
APPLICATIONS

None

FEDERALLY SPONSORED RESEARCH OR
DEVELOPMENT

None

PARTIES TO A JOINT RESEARCH
AGREEMENT

None

REFERENCE TO A SEQUENCE LISTING

None

BACKGROUND OF THE INVENTION

Technical Field of the Invention

The disclosure generally relates to syringes and a method of using the same, and more specifically to a multi-cycle syringe that will auto-disable.

Description of Related Art

The World Health Organization estimates, in fact sheet number 234, that twelve billion (12 billion) annual injections occur in developing and transitional nations. Many of these injections occur through the shared use of contaminated needles and syringe assemblies. Bloodborne diseases such as hepatitis B, hepatitis C and HIV/AIDS are transmitted through injections due to unsafe injection practices, such as the use of re-used contaminated needles and syringe assemblies. In many developing and transitional countries, the proportion of the population infected with hepatitis B and hepatitis C exceeds 10 times the prevalence seen in developed countries, and in many of these countries, unsafe injections account for a large proportion of new cases of infection. Thus, the cost of unsafe injection practices in developing countries is high.

One previous approach was to use a pre-filled single direction, single use syringe. A problem with this approach was that the syringe must be filled with a specific compound before being given to the medical professional.

Another approach was to use a syringe wherein the operator is required to physically break or disable the syringe assembly; however, an operator may not follow through with the disabling task.

Another approach was to use a syringe assembly with mechanics to destroy the syringe assembly, such as a stem that pierces a hole in syringe body; however such design may be circumvented as well.

Moreover, the above syringes designs limit the number of cycles or strokes of the syringe assembly to one (1) cycle or stroke before disabling and prohibit their use with medicines and vaccines distributed in a dehydrated and/or freeze dried form, whereby such dehydrated and/or freeze dried medicines and vaccines require a multi cycle syringe to load a wetting agent to activate the medicines and vaccines. It is important to note that such dehydrated and/or freeze dried medicines and vaccines are especially utilized in remote and difficult to reach developing and transitional nations due to their extended shelf life.

Therefore, it is readily apparent that there is a recognizable unmet need for a multi-cycle auto-disable device that is simple to setup, allows for multi-cycle operation, such as applying a wetting agent to dehydrated and/or freeze dried medications and vaccines, thereafter auto-disable, and provides an economically feasible syringe assembly, especially for developing and transitional nations to promote safe and sterile medical care.

SUMMARY

Briefly described, in a preferred embodiment, the present apparatus and method overcomes the above-mentioned disadvantages and meets the recognized need for such a device by providing a multi-cycle auto-disable device that is simple to setup, allows for multi-cycle operation, such as applying a wetting agent to dehydrated and/or freeze dried medications and vaccines, thereafter auto-disables, and provides an economically feasible syringe assembly, especially for developing and transitional nations to promote safe and sterile medical care.

The present apparatus and method includes a multi-cycle auto-disable syringe having a stem, container, and a plunger. The plunger includes at least one passageway or tube with a soluble substance therein that maintains a seal on compounds within the container's chamber, thus allowing a multi-cycle usage to dispense medication to patients, but further use with other patients is prevented after the soluble substance dissolves; thus, disabling the syringe.

According to its major aspects and broadly stated, the present disclosure describes a syringe device, wherein the syringe device has a stem, a plunger, and a container. The plunger has a passageway or tube filled with a soluble substance, and the container has a chamber sealed by the plunger, and the soluble substance prevents fluid and/or air communication between the chamber and the axial chamber.

The plunger also has a cover, such as a parabolic cover, and at least one tube positioned therethrough the plunger, the tube allows fluid and/or air communication between the chamber and the axial chambers when the cover is open and prevents fluid and/or air communication between the chamber and the axial chambers when the cover is closed. The plunger may also have a protrusion formed thereon, and the cover is integral to the protrusion and is further secured in a closed position to the perimeter of the plunger by the soluble substance.

Moreover, the stem may also have a secondary channel, and the secondary channel provides fluid communication between the chamber-plunger tube and the axial chambers. The plunger may also include a cavity, and the tube has a tube bottom, and the tube bottom is disposed at or near the cavity.

Alternatively, the plunger may also have a cover, such as a parabolic cover or other configured cover, and at least one tube positioned therethrough the plunger, the tube allows fluid and/or air communication between the chamber and the axial chambers when the cover is open and prevents fluid and/or air communication between the chamber and the axial chambers when the cover is closed wherein the cover may be form fitted or memory fitted thereto the plunger and the closed cover may require contact with a surface or object to open the cover or change its state and thus, disable the syringe.

The cover, such as a parabolic cover, is configured to stay in the open position but is forced into a closed or sealed position and may be held in place by the soluble substance acting as an adhesive. Once the bond of the adhesive has failed, the structure of the parabolic seal forces it to return to its original open position, enabling passageway between the chamber and the axial chambers.

Hydraulics/Hydrodynamics

The function of the syringe assembly is based on hydraulic and/or hydrodynamic principles based on the seal created between the plunger and body/container. The stem transfers external forces to the plunger. The linear motion of the stem and plunger, as a result of the external force, creates positive and negative hydraulic pressure in the forward cavity defined by the plunger and body/container. A forward motion of the stem and plunger creates a positive pressure in the forward cavity and is the positive pressure that forces the injection material (fluid and/or air) contained in the forward cavity to exit the forward cavity and travel through the small orifice of the needle. Conversely, a rearward motion or retraction of the stem and plunger pulls the plunger backwards creating a negative pressure in the forward cavity and is the negative pressure that pulls the injection material (fluid and/or air) into the forward cavity through the small orifice of the needle to fill the forward cavity. During the linear motion of the stem and plunger assembly the plunger maintains a seal between the plunger and the sidewall of the container/body. This seal is critical to the creation and control of the hydraulic pressure differentials created in the forward cavity to move injection material (fluid and/or air) in and out of the forward cavity.

Multi-Cycle Sequence

In use, for example, the syringe is injected into a vial holding suspension media. Next, the stem is pushed inward to create positive pressure inside the vial of suspension media, and then the stem is pulled outward to draw the suspension media into the syringe, and the soluble substance begins dissolving. Next, the stem is pushed inward to inject the suspension media into a vial of dried medication or vaccine, and then the stem is pulled outward to draw the medication now in suspension into the syringe. Subsequently, the stem is pushed inward to inject the medication into a patient. Next, the soluble substance dissolves, after which the chamber or forward cavity and the axial chambers are in fluid communication; thus, disabling plunger from creating positive or negative hydraulic pressure in the forward cavity defined by the plunger and body/container.

Injection material, such as a fluid, entry into forward cavity defined by the plunger and body/container, more specifically when the injection material comes in contact with the soluble substance; this starts the clock for auto-disable function of the syringe. Once the soluble substance is dissolved the syringe is disabled. The soluble characteristics of the soluble substance, whether adhesive bond, mechanical bond, or mechanical block, determines the rate and/or time of deterioration and failure of the forward cavity seal defined by the plunger and body/container rendering the syringe unusable. The time the syringe is functional and the number of cycles of use the syringe may accomplish is determined by the rate of deterioration. Controlling the deterioration of the soluble substance blocking the secondary passageway that circumvents the seal defined by the plunger and body/container enables a designer to set the time of use or number of cycles of use for the syringe. The disable time is defined as the time required for the soluble substance to dissolve unblocking the secondary passageway that circumvents the seal defined by the plunger and body/container, or the time required to deteriorate soluble substance holding the cover in its closed position. Using soluble substance allows for exposure of the injection material (fluid medium) being dispensed or injected by the syringe to be the controlling agent or event to start the deterioration of the soluble substance. Therefore, by varying the composition of the soluble substance this controls the rate of deterioration and thus the cycle count and usage time of the syringe allowing cycling of the syringe more than one time, such as when using a dried vaccine or material that requires the introduction of a re-hydrating agent.

In another embodiment, the syringe has a stem, a plunger, and a container. The stem has a depresser, the plunger has a soluble substance, and the container has a chamber. The soluble substance prevents fluid communication between the chamber and the depresser. The plunger also has a tube and a cavity, and the tube has a tube bottom, the tube bottom being at or near the cavity. The stem also has a secondary channel. The stem also has a base, the base having a base top. The base is preferably located within or near cavity. The base top is disposed proximate the tube bottoms when the stem is being pushed inward.

The soluble substance is any substance or compound as known in the art that will dissolve under the circumstances described herein, including, for exemplary purposes and without limitation, a natural or organic based adhesive such as potato starch, a sugar and water mixture, a mechanical binder such as that used to bind aspirin in pill form, or the like. Moreover, the soluble substance may dissolve over a period of time after coming into contact with compound, medication, and its mixture, such as suspension media, and/or wetting agent or medication, such that preferably the substance dissolves within a predetermined time, such as minutes.

In an alternate embodiment, the plunger also has a cover, and the tube further has a tube top. The cover is initially secured to the stem by the soluble substance, and the secured cover prevents fluid communication between the tube and the chamber. The stem has an axial chamber and a secondary channel.

More specifically, the present disclosure of a preferred embodiment is a syringe, the syringe having a stem and a container. The stem has a plunger, axial supports, axial chambers, secondary channels, a depresser, and a base, the depresser having a depresser diameter, and the base having a base diameter and a base top, and the axial supports having axial chambers. The container has a lip, a chamber, a bottom, a sidewall, a container diameter, and an extruder, the extruder having a channel. The plunger has a plunger diameter, a cover, a bottom interior periphery, a bottom inner diameter, a bottom outer diameter, a bottom exterior periphery, a tube, and a protrusion, the tube having a tube bottom, a tube top, and a soluble substance, and the protrusion has a plunger top and a protrusion diameter, and the cover has a cover periphery. The chamber preferably includes a compound, which includes medication, suspension medication, and dried medication, and may include air before use has been initiated.

The plunger is preferably fixedly secured to the base of the stem. The axial chambers are disposed between the axial supports, the axial supports being disposed between the base and the depresser. The extruder extends from the container, and the compound is ejected from the container via the extruder channel, which preferably has a tubular needle attached through which the compound preferably flows into a patient or into a vial.

The cover is disposed above and attached to the protrusion, and when the cover is open then the cover does not prevent fluid connectivity between the tubes and the chamber, and the stem is disposed within the plunger.

When the cover is closed, it smothers or covers the tubes, therein preventing any fluid and/or air from transiting from the cavity through the tubes. The tubes are may also be filled with the soluble substance.

The plunger is disposed upon the stem within the container. The base is disposed within the cavity. When the stem is pushed into the container, the base top of the stem is disposed against the tube bottom of the tubes, thus preferably preventing fluid communication between the cavity and the chamber and enabling positive pressure in the cavity. When the stem is pulled from the container, the base is disposed against the bottom interior periphery enabling fluid communication between the cavity and the chamber and disabling negative pressure in the cavity.

In one embodiment, the protrusion on the plunger is substantially flat. The bottom exterior periphery of the plunger extends around the bottom interior periphery, and the bottom inner diameter is the greatest distance between any two points on the bottom interior periphery. The tubes are preferably, although not necessarily, filled with a soluble substance, thereby preventing liquid communication between the chamber and cavity. When the cover is closed, the cover is also preventing liquid communication between the chamber and cavity.

In use, the syringe is injected into a vial holding suspension media. Next, the stem is pushed inward to create positive pressure inside the vial of suspension media. Subsequently, the stem is pulled outward creating a negative pressure in the syringe to draw suspension media into the syringe. Concurrently, the soluble substance begins decomposing. The stem is pushed inward creating a positive pressure inside the syringe to inject suspension media in the vial of dried medication. Subsequently, the stem is pulled outward creating a negative pressure in the syringe to draw medication into the syringe. The stem is then pushed inward to create positive pressure inside the syringe to inject medication into the patient. Finally, at some point the substance dissolves, thus the cavity and chamber are in fluid communication preventing hydraulic pressure in the syringe chamber.

When the soluble substance at the cover periphery fully dissolves, the cover opens preventing hydraulic pressure in the syringe chamber. This is because the cover is naturally disposed towards the depiction shown when the cover is open, but the soluble substance holds the cover down enabling hydraulic pressure in the syringe chamber. Subsequently, the soluble substance in the tubes dissolves, thus the cavity and chamber are in fluid communication. However, even when the cover and the tubes are open, fluid communication between chamber and cavity may be temporarily interrupted when the stem is moved inward, thus disposing the base top in contact with tube bottom, which temporarily seals the tubes. Thus, allowing for positive pressure in the cavity in the inward direction only and allowing medication resident in the chamber to be discharged from the syringe.

Syringe may not include a cover, in which case the soluble substance in the tubes is the only object preventing fluid communication between the cavity and chamber. Alternatively, the syringe may have a cover, and the tubes may not be filled with a soluble substance, in which case the cover is the only object preventing fluid communication between the cavity and chamber.

Preferably, the medication is dispensed from the chamber before the chamber and cavity are in fluid communication. However, as long as the chamber and cavity are not in fluid communication, the action of pushing the stem inward will force the plunger top against the tube bottoms, thus temporarily preventing fluid communication while medication is injected into the patient.

When the chamber and cavity are in fluid communication, the chamber and axial chambers are also in fluid communication. Accordingly, when the stem is pulled outward, the chamber can be filled from air that was within the axial chambers, thus preventing and/or interfering with compound attempting to be pulled into the chamber via the tubular needle. In this situation, the syringe has been disabled and therefore syringe is incapable of further use, and thus, incapable of assisting the further spread of communicable diseases and viruses, excepting that the syringe can still dispense the compound within it, as described elsewhere.

It will be recognized that the axial chambers may be any configuration that allows for fluid communication between secondary channels and atmospheric air that generally surrounds the outside of the syringe, such as, for exemplary purposes only, the atmospheric air disposed near the depresser. Similarly, it will be recognized that secondary channels may be in any configuration that allows for fluid communication between the chamber and axial chambers. Further, it will be recognized that the tubes may be any configuration that allows for fluid communication between the chamber and axial chamber.

Accordingly, a feature of the multi-cycle auto-disable device is its ability to allow any type of compound to be dispensed.

Another feature of the multi-cycle auto-disable device is its ability to be relatively easy to manufacture and is not cost prohibitive utilizing a high percentage of existing tooling and manufacturing processes.

Yet another feature and advantage of the multi-cycle auto-disable device is its ability to be transparent in application to the end user requiring no action other than normal use to be activated.

Yet another feature and advantage of the multi-cycle auto-disable device is its ability to not require any action by the user to initiate function.

Yet another feature and advantage of the multi-cycle auto-disable device is its ability to not be circumvented by the user.

Yet another feature and advantage of the multi-cycle auto-disable device is its ability to not require being pre-filled.

Still another feature of the multi-cycle auto-disable device is its ability to be easy to use requiring minimal education and/or training of the user.

Yet another feature of the multi-cycle auto-disable device is its ability to continue to be used for one complete multi-cycle use and then auto-disable to prevent further uses.

Yet another feature of the multi-cycle auto-disable device is its ability to help prevent the spread of infectious diseases.

These and other features of the multi-cycle auto-disable device will become more apparent to one skilled in the art from the prior Summary, and following Brief Description of the Drawings, Detailed Description, and Claims when read in light of the accompanying Detailed Drawings.

BRIEF DESCRIPTION OF THE DRAWINGS

The present multi-cycle auto-disable device will be better understood by reading the Detailed Description with reference to the accompanying drawings, which are not necessarily drawn to scale, and in which like reference numerals denote similar structure and refer to like elements throughout, and in which.

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure, as illustrated in FIGS. 1-10, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Referring now to FIGS. 1-10 by way of example, and not limitation, therein is illustrated an example embodiment syringe 100, wherein syringe 100 comprises stem 200 and container 400. Stem 200 comprises plunger 300, axial supports 210, axial chamber 220, secondary channel 250, depresser 230, and base 240, wherein depresser 230 comprises stem diameter 215, and wherein base 240 comprises base diameter 245 and base top 247, and axial supports 210 comprise axial chambers 220. Container 400 comprises lip 410, bottom 420, sidewall 440, container diameter 450, chamber 460, and extruder 430, wherein extruder 430 comprises extruder channel 435. Plunger 300 comprises plunger diameter 305, cover 320, bottom interior periphery 350, bottom inner diameter 355, bottom outer diameter 357, bottom exterior periphery 360, tube 330, and protrusion 340, wherein tube 330 comprises tube bottom 332, tube top 334, and substance 335, and wherein protrusion 340 comprises plunger top 342 and protrusion diameter 345, and wherein cover 320 comprises cover periphery 322. Chamber 460 preferably comprises compound C, which comprises medication M, suspension medication SM, and dried medication DM.

Figure 1:
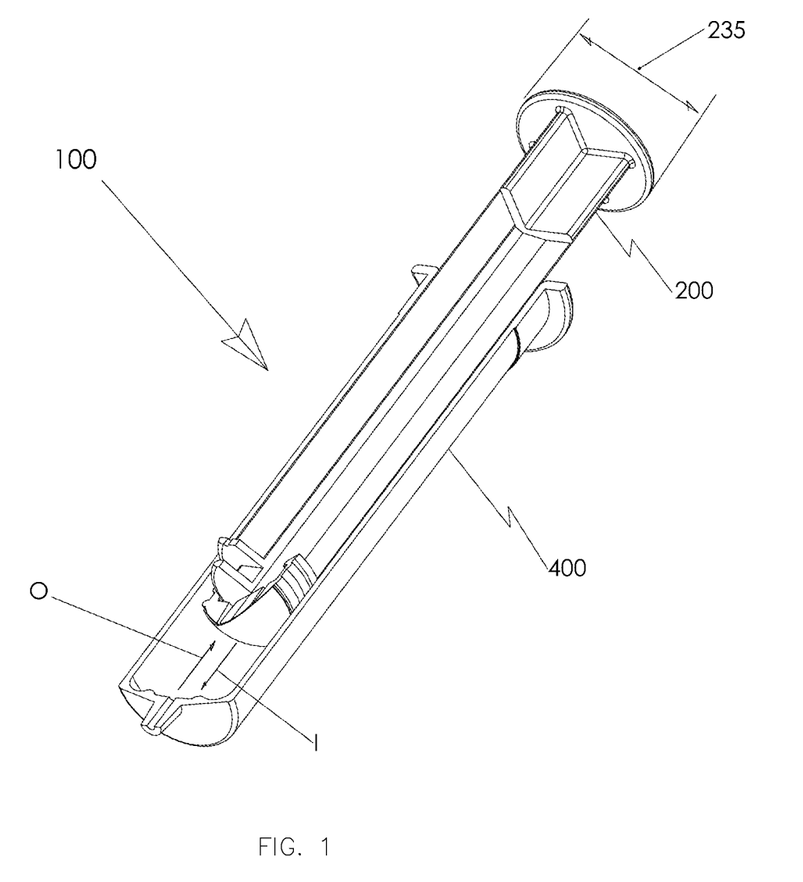
FIG. 1 is a perspective view of an exemplary embodiment of the syringe assembly.
Figures 2, 2B:
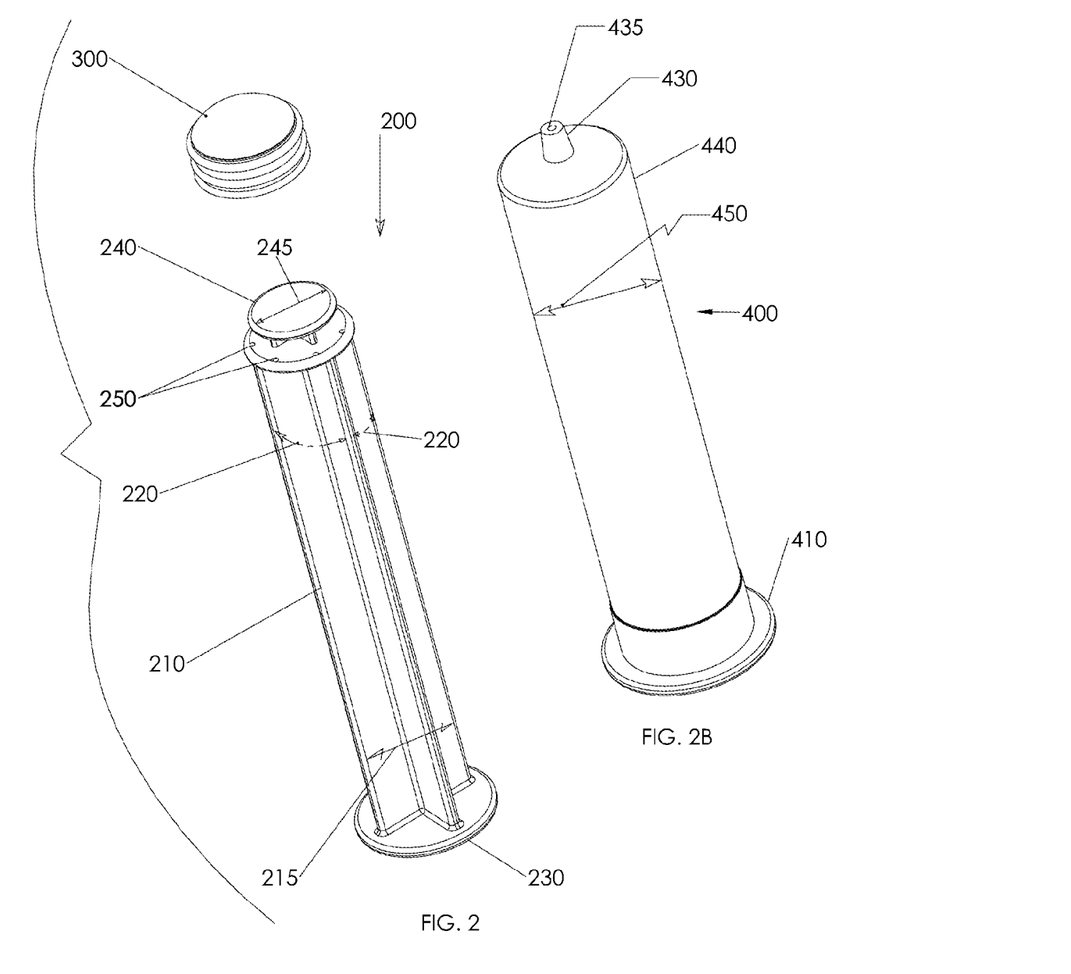
FIG. 2 is a separated perspective view of the stem of the exemplary embodiment of FIG. 1.
FIG. 2B is a perspective view of an embodiment of the body or container of the exemplary embodiment of FIG. 1.

Turning now to FIGS. 1-2B, stem 200 is inserted within container 400. Stem 200 can be moved within container 400 either via inward I direction or outward O direction. Plunger 300 is preferably narrower than container diameter 450 (best shown in FIG. 1), thus enabling plunger 300 and stem 200 to fit therein and travel out O or in I container 400. Moreover, plunger 300 divides container 400 into chamber 460 and axial chamber 220 and plunger 300 travel in and out of container 400 is preferably identified as in I and out O travel of stem 200 and plunger 300 of container 400.

Turning more particularly to FIG. 2, plunger 300 is preferably removably secured to base 240 of stem 200. Axial chambers 220 are disposed between axial supports 210, wherein axial supports 210 are disposed between base 240 and depresser 230. Turning now to FIG. 2B, extruder 430 extends from container 400, wherein compound C is ejected from container 400 via extruder channel 435, which preferably has a tubular needle attached (not shown) through which compound C flows. It will be recognized that this tubular needle could be any device as used in the medical profession to inject into or withdraw from patients medication, blood, or other substances.

It is contemplated herein that axial chambers 220 function as any type of structure that will allow fluid communication between chamber 460 and atmospheric conditions, wherein said fluid communication is preferably, although not necessarily, via cavity 380 and secondary channel 250. Thus axial chambers 220 may be any structure such as, for exemplary purposes only and without limitation, a lattice type structure, a series of triangular shapes with fluid communication enablement, a series of structural beams, a sponge-like material, or the like that allows fluid communication as herein described.

Figure 3A:
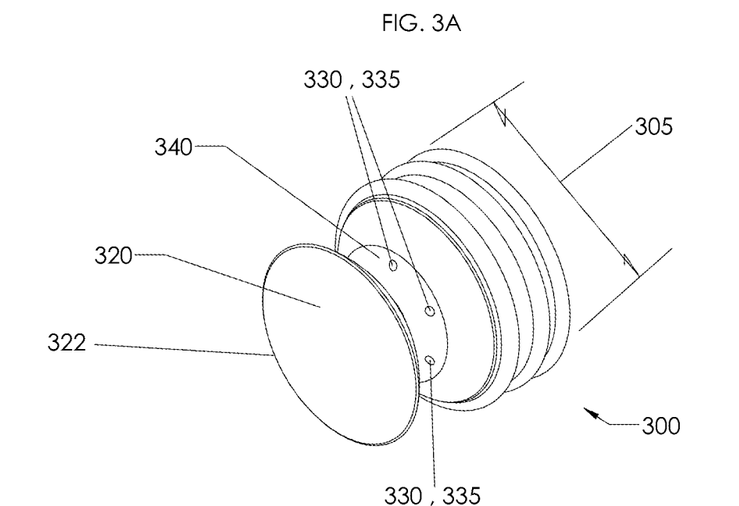
FIG. 3A is a perspective view of the plunger of the exemplary embodiment of FIG. 1, with the cover in an open position.
Figures 3B, 3C:
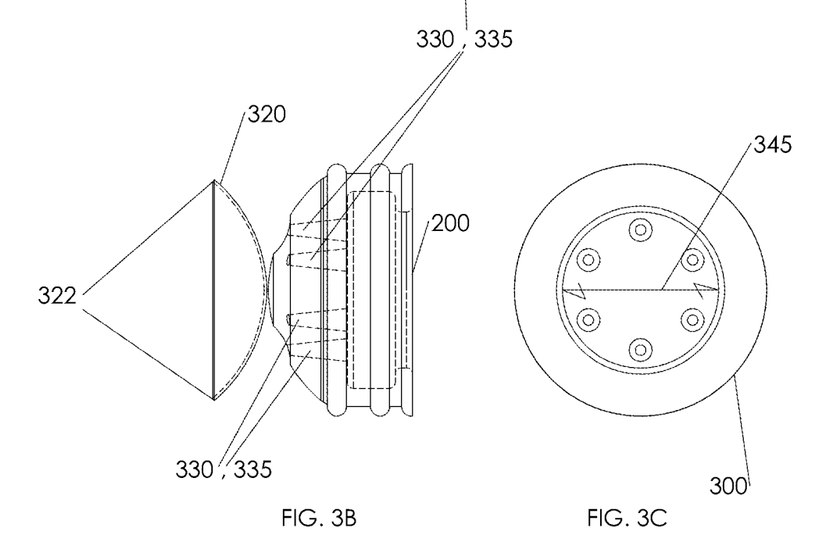
FIG. 3B is a side view of the plunger of the exemplary embodiment of FIG. 1, with the cover in an open position.
FIG. 3C is a top view of the plunger of the exemplary embodiment of FIG. 1.

Turning now to FIGS. 3A-3C, illustrated therein is plunger 300, wherein cover 320 is open. Tubes 330 may be filled with substance 335. Cover 320 is disposed above and attached to protrusion 340, wherein when cover 320 is open then cover 320 does not prevent fluid connectivity between tubes 330 and chamber 460 (best shown in FIGS. 3A and 6); thus, exposing tubes 330 to compound C and/or disabling compression, discharge or to draw in, suction of compound C by syringe 100, when stem 200 and plunger 300 travel out O or in I, respectively, of container 400 (shown in FIG. 1). Turning more particularly to FIG. 3B, stem 200 is disposed within plunger 300 and tubes 330 preferably configured to define a passageway therethrough plunger 300, such as between chamber 460 (shown in FIGS. 1, 3A and 6) and axial chamber 220 of container 400.

It is contemplated herein that plunger 300 may be operational without cover 320, wherein tubes 330 are preferably filled with a substance 335 (shown in FIG. 8B) capable of dissolving or timed dissolving when in contact with compound C. Once substance 335 has dissolved tubes 330 define a passageway therethrough plunger 300, such as between chamber 460 (shown in FIGS. 1, 3A and 6) and axial chamber 220 (shown in FIG. 1) of container 400 disabling compression, discharge or to draw in, suction of compound C by syringe 100, when stem 200 and plunger 300 travel out O or in I, respectively, of container 400 (shown in FIG. 1).

It is contemplated herein that tubes 330 are preferably configured as conical shaped, preferably narrower circumference on chamber 460 (shown in FIGS. 1, 3A and 6) side and broader circumference on axial chamber 220 (shown in FIG. 1) side to enable efficient dislodge of particulates, such as substance 335, within tubes 330.

It is contemplated herein that other configurations of tubes 330, which are preferably configured to define a passageway therethrough plunger 300.

It is further contemplated herein that protrusion 340 is curved or contoured and may have a matching bottom 420 of container 400. In operation, when stem 200 and plunger 300 travel in I container 400 wherein protrusion 340 contacts matching bottom 420, matching bottom 420 pries or dislodges cover 320 form plunger 300 to insure cover 320 is open.

Figures 4A, 4C:
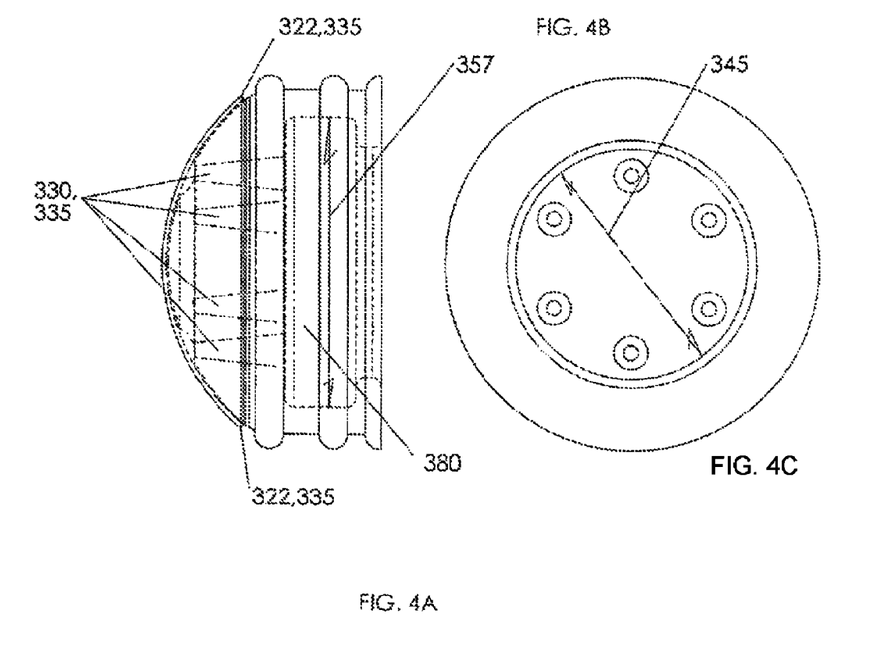
FIG. 4A is a side view of the plunger of a different exemplary embodiment, with the cover in a closed position.
FIG. 4C is a top view of the plunger of a different exemplary embodiment, with the cover in a closed position.
Figure 4B:
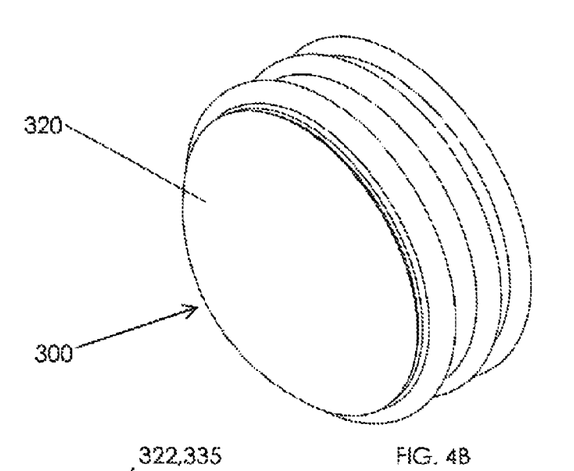
FIG. 4B is a perspective view of the plunger of a different exemplary embodiment, with the cover in a closed position.

Turning now to FIGS. 4A-4C, illustrated therein is another embodiment of plunger 300, wherein cover 320 is closed, and wherein cover 320 is generally parabolic, and wherein cover 320 is integrated to protrusion 340, and wherein cover 320 is secured to plunger periphery 322 by substance 335. When cover 320 is closed, cover 320 smothers or covers tubes 330, enabling compression, discharge or to draw in, suction of compound C by syringe 100, when stem 200 and plunger 300 travel out O or in I, respectively, of container 400 (shown in FIG. 1). Turning more particularly to FIG. 4A, tubes 330 preferably configured to define a passageway therethrough plunger 300, such as between chamber 460 (shown in FIGS. 1, 3A and 6) and axial chamber 220 (shown in FIG. 1) of container 400.

It is contemplated herein that cover 320 is preferably releasably affixed to cover periphery 322 of plunger 300 by substance 335 capable of dissolving or timed dissolving when in contact with compound C. Once substance 335 has dissolved cover 320 is released and returns to open, as shown in FIG. 3, disabling compression, discharge or to draw in, suction of compound C by syringe 100, when stem 200 and plunger 300 travel out O or in I, respectively, of container 400 (shown in FIG. 1). Cover 320, is configured to stay in the open position but is forced into the closed or sealed position by substance 335.

Alternatively, cover 320 may be form fitted or memory fitted thereto plunger 300 and closed cover 320 may require contact with a surface or object to open the cover or change its state and thus, disable syringe 100.

It is contemplated herein that in some embodiments tubes 330 are filled with substance 335 and in some other embodiments tubes 330 are not filled with substance 335.

Figure 5:
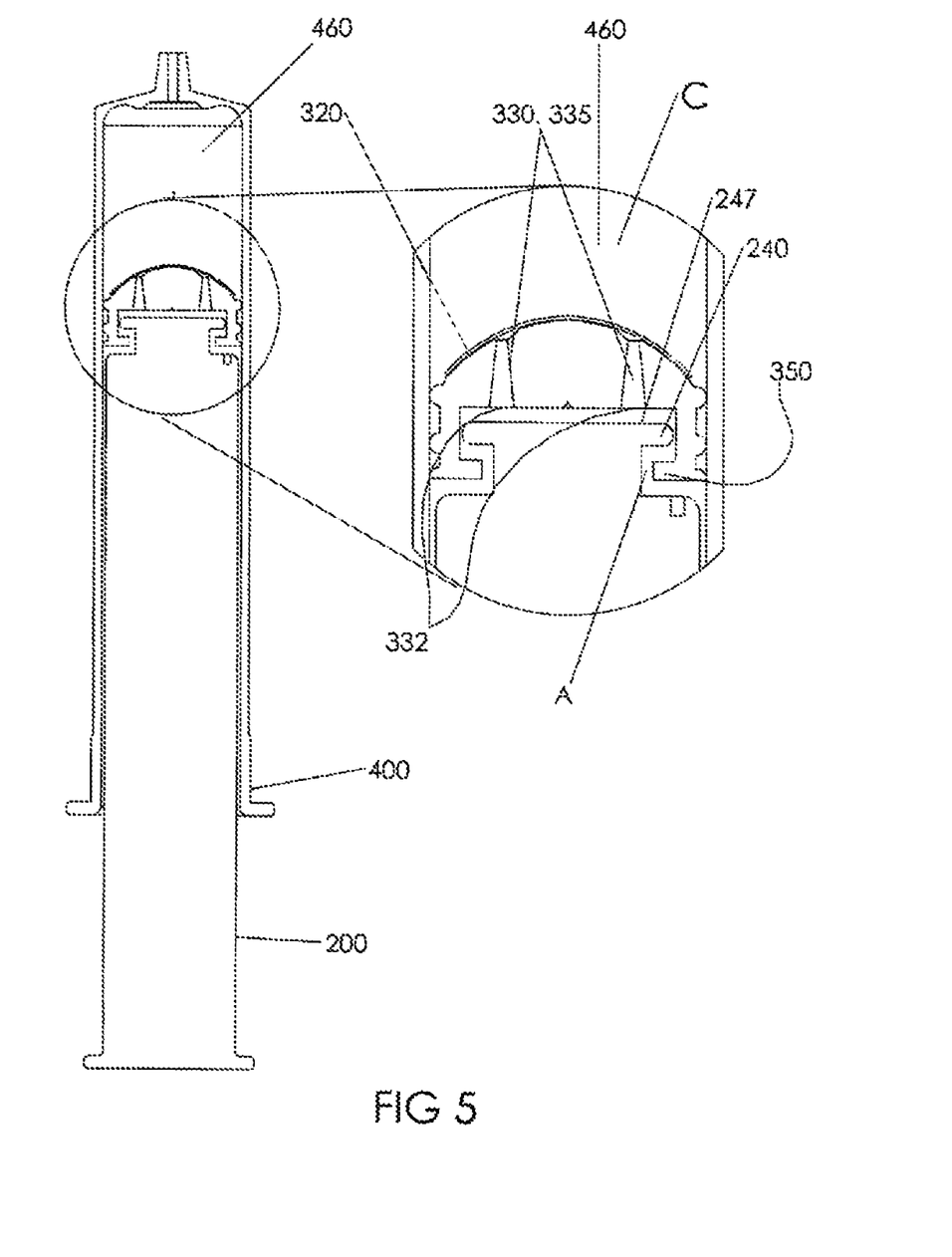
FIG. 5 is an exploded view of the plunger of an exemplary embodiment, with the cover in a closed position.

Turning now to FIG. 5, pictured therein is an expanded view of plunger 300 disposed upon stem 200 within container 400, wherein cover 320 is closed. In the exemplary embodiment shown, base 240 is disposed within cavity 380. When stem 200 is pushed into container 400, plunger 300 travels in I into container 400 (shown in FIG. 1) enabling compression, discharge of compound C from extruder channel 435 of extruder 430. Further, on the shown embodiment, plunger diameter 305 is proximately equal to container diameter 450, thus preventing compound C from exiting chamber except through either extruder channel 435 or tubes 330.

It is contemplated herein that base diameter 245 is preferably less than bottom out diameter 357 (best shown in FIG. 4A), thus enabling a passageway therethrough plunger 300 such as between chamber 460 (shown in FIGS. 1, 3A and 6) and axial chamber 220 (shown in FIG. 1) of container 400 via tubes 330 and passage way shown by air A.

It is contemplated herein an alternate embodiment that when plunger 300 travels in I into container 400 base top 247 of base 240 is disposed against tube bottom 332 of tubes 330, thus preferably preventing fluid communication between cavity 380 and chamber 460 or disabling a passageway therethrough plunger 300 such as between chamber 460 (shown in FIGS. 1, 3A and 6) and axial chamber 220 (shown in FIG. 1) of container 400 via tubes 330 and passage way shown by air A. Such configuration enables a single discharge syringe 100 because of positive pressure being created in chamber 460 by motion inward I of plunger 300.

Figure 6:
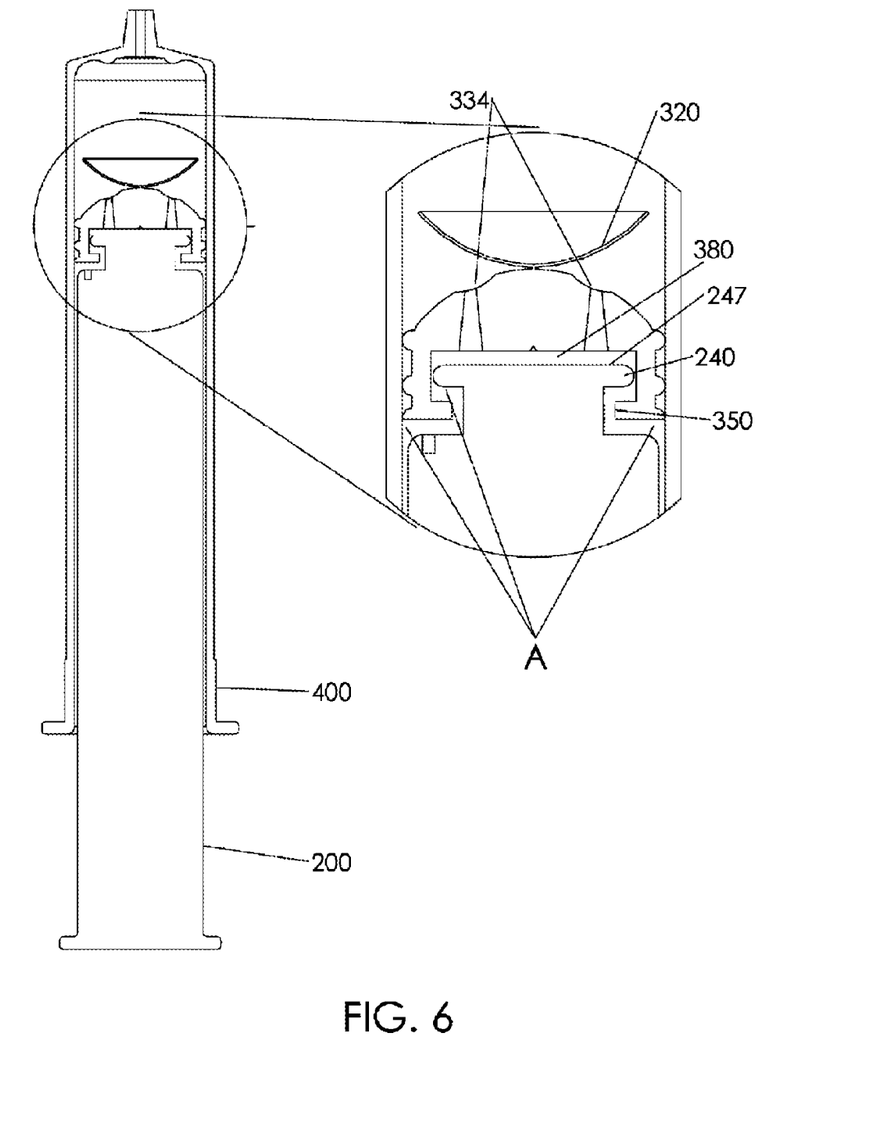
FIG. 6 is an exploded view of the plunger of an exemplary embodiment, with the cover in an open position.

Turning now to FIG. 6, pictured therein is an expanded view of plunger 300 disposed upon stem 200 within container 400, wherein cover 320 is open. When cover 320 is open, cover 320 no longer smothers or covers tube top 334 of tubes 330, wherein air A within cavity 380 is fluidly connected to chamber 460. When stem 200 is pulled from container 400 plunger 300 travels out O of container 400 (shown in FIG. 1) disabling the drawing in or suction of compound C into extruder channel 435 of extruder 430 and/or the disabling of compression, discharge of compound C from extruder channel 435 of extruder 430. Syringe 100 is disabled because fluid communication between cavity 380 and chamber 460 prevents the creation of negative pressure in chamber 460.

It is contemplated herein that base diameter 245 is preferably less than bottom out diameter 357 (best shown in FIG. 4A), thus enabling a passageway therethrough plunger 300 such as between chamber 460 (shown in FIGS. 1, 3A and 6) and axial chamber 220 (shown in FIG. 1) of container 400 via tubes 330 and passage way shown by air A.

It is contemplated herein that an alternate embodiment plunger 300 may travel out O from container 400 base top 247 of base 240 is removed from tube bottom 332 of tubes 330, thus preferably enabling fluid communication between cavity 380 and chamber 460 and/or enabling a passageway therethrough plunger 300 such as between chamber 460 (shown in FIGS. 1, 3A and 6) and axial chamber 220 (shown in FIGS. 1) of container 400 via tubes 330 and passage way shown by air A.

It is further contemplated herein that if tubes 330 are filled with a substance 335 (shown in FIG. 8B) capable of dissolving or timed dissolving when in contact with compound C that once substance 335 has dissolved tubes 330 and passage way shown by air A define a passageway therethrough plunger 300, such as between chamber 460 (shown in FIGS. 1, 3A and 6) and axial chamber 220 (shown in FIG. 1) of container 400 disabling compression, discharge or to draw in, suction of compound C by syringe 100, when stem 200 and plunger 300 travel out O or in I, respectively, of container 400 (shown in FIG. 1).

Figure 7A:
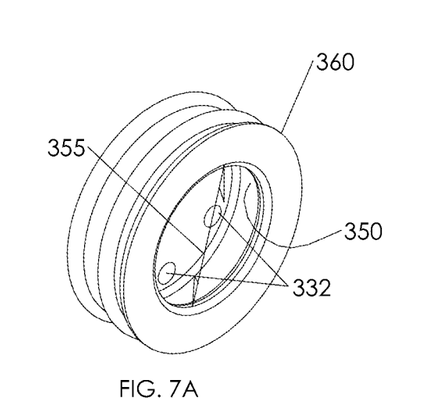
FIG. 7A is a perspective view of the plunger of a different exemplary embodiment, with the cover in a closed position.
Figure 7B:
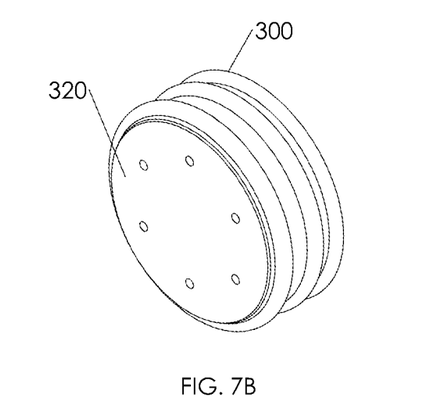
FIG. 7B is a perspective view of the plunger of the exemplary embodiment of FIG. 7A, with the cover in a closed position.

Turning now to FIGS. 7A-8B, illustrated therein is an alternate embodiment of plunger 300, wherein protrusion 340 is substantially flat (best shown in FIG. 8B), and wherein cover 320 is closed. Turning more particularly to FIG. 7A, bottom exterior periphery 360 of plunger 300 extends around bottom interior periphery 350, wherein bottom inner diameter 355 is the greatest distance between any two points on bottom interior periphery 350. Tubes 330 are preferably, although not necessarily, filled with substance 335, thereby preventing liquid communication between chamber 460 and cavity 380. When cover 320 is closed, cover 320 is also preventing liquid communication between chamber 460 and cavity 380.

It is contemplated herein that when cover 320 is preferably releasably affixed to cover periphery 322 of plunger 300 by substance 335, is closed, cover 320 smothers or covers tubes 330 blocking passage therethrough tubes 330, thus enabling compression, discharge or to draw in, suction of compound C by syringe 100, when stem 200 and plunger 300 travel out O or in I, respectively, of container 400 (shown in FIG. 1).

Figure 8A:
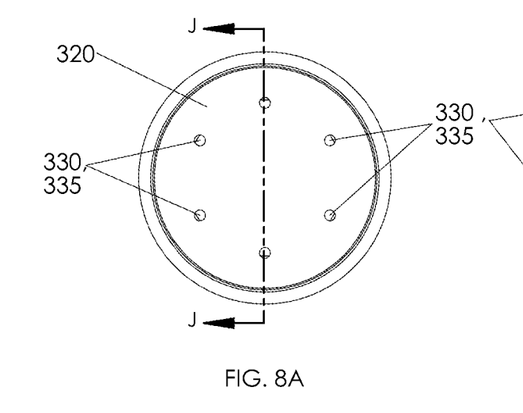
FIG. 8A is a top view of the plunger of the exemplary embodiment of FIG. 7A, with the cover in a closed position.
Figure 8B:
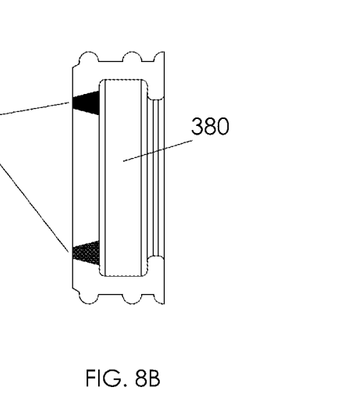
FIG. 8B is a side view of the plunger of the embodiment of FIG. 8A, shown along the line labeled JJ in FIG. 8A.

Turning more particularly to FIG. 8A-8B, tubes 330 preferably configured to define a blocked passageway therethrough plunger 300, such as between chamber 460 (shown in FIGS. 1, 3A and 6) and axial chamber 220 (shown in FIG. 1) of container 400. It is contemplated herein that cover 320 is preferably releasably affixed to cover periphery 322 of plunger 300 by substance 335 and tubes 330 are preferably filled with substance 335, thus enabling compression, discharge or to draw in, suction of compound C by syringe 100, when stem 200 and plunger 300 travel out O or in I, respectively, of container 400 (shown in FIG. 1).

Figure 9:
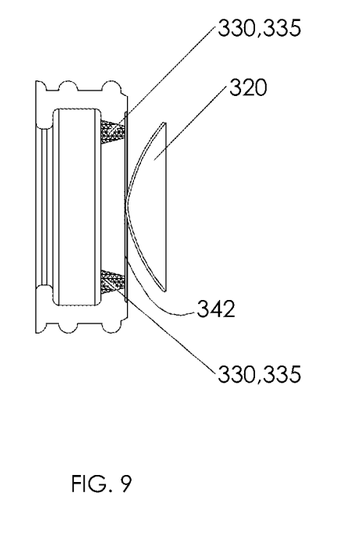
FIG. 9 is a top view of a portion of a different exemplary embodiment, with the cover in an open position.

Turning now to FIGS. 9A-9B, illustrated therein is a different embodiment of plunger 300, wherein protrusion 340 is substantially flat (best shown in FIG. 9B), and wherein cover 320 is open. Tubes 330 are preferably, although not necessarily, filled with substance 335, thereby preventing liquid communication between chamber 460 and cavity 380. When cover 320 is open, cover 320 is not preventing liquid communication between chamber 460 and cavity 380.

Once substance 335 has dissolved cover 320 is released and returns to open, as shown in FIGS. 3 and 6, and once substance 335 has dissolved from tubes 330 to define a passageway therethrough plunger 300, such as between chamber 460 (shown in FIGS. 1, 3A and 6) and axial chamber 220 (shown in FIG. 1) of container 400, thus disabling compression, discharge or to draw in, suction of compound C by syringe 100, when stem 200 and plunger 300 travel out O or in I, respectively, of container 400 (shown in FIG. 1).

When in use, stem 200 transfers external forces to plunger 300. The linear motion inward I and outward O of stem 200 and plunger 300, create positive and negative hydraulic pressure in chamber 460. Motion inward I of plunger 300 creates a positive pressure in chamber 460, thus forcing the extrusion of compound C or air A through extruder channel 435, and subsequently the small orifice of a needle (not shown). Motion outward O of plunger 300 creates a negative pressure in chamber 460, thus forcing the intake of compound C or air A through extruder channel 435. During both motion inward I and outward O, plunger periphery 322 maintains a seal with the interior of sidewall 440 of container 400. This seal allows for the positive and negative pressure to force the ejection or intake of compound C or air A.

Figure 10:
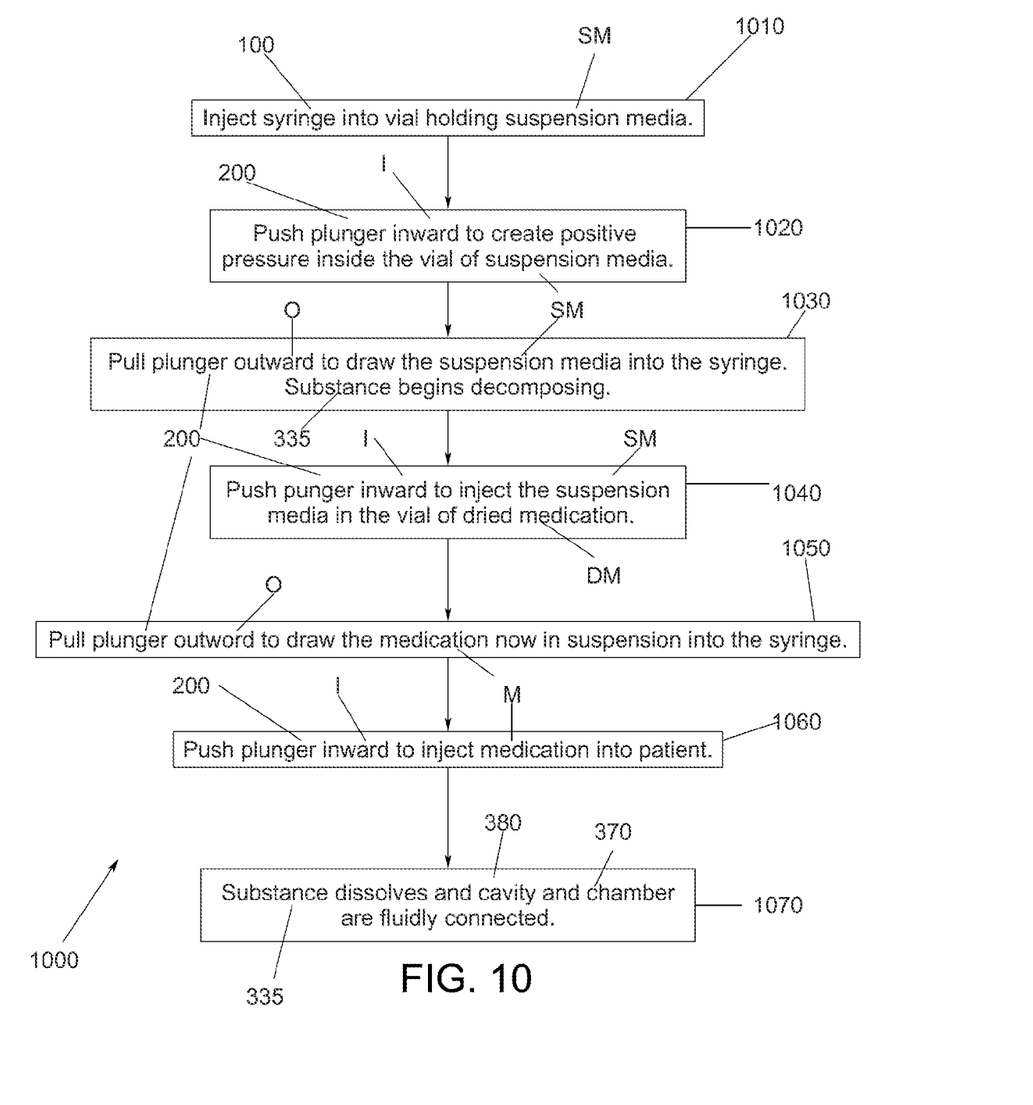
FIG. 10 is a flow chart depicting an exemplary use of an embodiment.

Turning now to FIG. 10, method of using syringe 1000 comprises injecting syringe 100 into a vial holding suspension media SM via step 1010. Via step 1020, stem 200 is pushed in or inward I to create positive pressure inside the vial of suspension media SM. Subsequently, via step 1030, stem 200 is pulled out or outward O, creating negative pressure in chamber 460, to draw suspension media SM into syringe 100. Concurrently, substance 335 begins decomposing. Via step 1040, stem 200 is pushed in or inward I, creating positive pressure in chamber 460, to inject suspension media SM in the vial of dried medication DM, which may comprise a vaccine. Subsequently, stem 200 is pulled out or outward O, creating negative pressure in chamber 460, to draw medication M into syringe 100, via step 1050. Stem 200 is then pushed in or inward I, creating positive pressure in chamber 460, to inject medication M into the patient, via step 1060. Finally, via step 1070, substance 335 dissolves, thus cavity 380 and chamber 460 become fluidly connected; thus, disabling plunger 300 from creating positive or negative hydraulic pressure in chamber 460 defined by plunger 300 and container 400.

The soluble characteristics of substance 335, whether adhesive bond, mechanical bond, or mechanical block, define the rate and/or time of deterioration and failure of seal of chamber 460. The time syringe 100 is functional and the number of cycles syringe 100 may accomplish is determined by the rate of deterioration. Controlling the deterioration time allows the designer and/or manufacturer of syringe 100 to set the time of use or the number of cycles.

When substance 335 fully dissolves, via step 1070, substance 335 at cover periphery 322 releases cover 320, thus, cover 320 opens (best shown in FIG. 6). Subsequently, substance 335 in tubes 330 dissolves, thus fluidly connecting cavity 380 and chamber 460. However, even when cover 320 and tubes 330 are open, fluid communication between chamber 460 and cavity 380 may be temporarily interrupted when stem 200 is moved in or inward I, thus disposing base top 247 in contact with tub bottom 332 (best shown in FIG. 6).

Moreover, once substance 335 has dissolved cover 320 is released and returns to open, as shown in FIGS. 3 and 6, and/or once substance 335 has dissolved from tubes 330 to define a passageway therethrough plunger 300, such as between chamber 460 (shown in FIGS. 1, 3A and 6) and axial chamber 220 (shown in FIG. 1) of container 400, thus disabling compression, discharge or to draw in, suction of compound C by syringe 100, when stem 200 and plunger 300 travel out O or in I, respectively, of container 400 (shown in FIG. 1).

It will be recognized that in an alternate embodiment, syringe 100 does not comprise cover 320, in which case substance 335 in tubes 330 is the only object preventing fluid communication between cavity 380 and chamber 460.

Once substance 335 has dissolved from tubes 330 to define a passageway therethrough plunger 300, such as between chamber 460 (shown in FIGS. 1, 3A and 6) and axial chamber 220 (shown in FIG. 1) of container 400, thus disabling compression, discharge or to draw in, suction of compound C by syringe 100, when stem 200 and plunger 300 travel out O or in I, respectively, of container 400 (shown in FIG. 1).

Alternatively, syringe 100 may comprise cover 320, but tubes 330 may not comprise substance 335, in which case cover 320 is the only object constantly preventing fluid communication between cavity 380 and chamber 460.

Once substance 335 has dissolved cover 320 is released and returns to open, as shown in FIGS. 3 and 6, tubes 330 define a passageway therethrough plunger 300, such as between chamber 460 (shown in FIGS. 1, 3A and 6) and axial chamber 220 (shown in FIG. 1) of container 400, thus disabling compression, discharge or to draw in, suction of compound C by syringe 100, when stem 200 and plunger 300 travel out O or in I, respectively, of container 400 (shown in FIG. 1).

Preferably, medication M is dispensed from chamber 460 before chamber 460 and cavity 380 are fluidly connected. However, in an exemplary embodiment, the action of pushing stem 200 in or inward I will force base top 247 against tube bottoms 332, thus temporarily preventing fluid communication between chamber 460 and axial chambers 220 while medication M is being injected into the patient.

Substance 335 is a compound that will dissolve over a period of time after coming into contact with medication M, suspension media SM, and/or dried medication DM, such that preferably substance 335 dissolves within a predetermined time, such as within several minutes.

Turning back to FIG. 2, when chamber 460 and cavity 380 are in fluid communication, chamber 460 and axial chambers 220 are also in fluid communication. Accordingly, when stem 200 is pulled out or outward O, chamber 460 can be filled from air A that is within axial chambers 220, thus preventing and/or interfering with compound C being pulled into chamber 460 via the tubular needle. In this situation, syringe 100 has been disabled and therefore syringe 100 is incapable of further use, and thus, incapable of assisting the further spread of communicable diseases and viruses.

It will be recognized that axial chambers 220 may be any configuration that allows for fluid communication between secondary channels 250 and atmospheric air that generally surrounds the outside of syringe 100, such as, for exemplary purposes only, the atmospheric air disposed near depresser 230. Similarly, it will be recognized that secondary channels 250 may be in any configuration that allows for fluid communication between chamber 460 and axial chambers 220. Also similarly, it will be recognized that tubes 330 may be any configuration that allows for fluid communication between chamber 460 and axial chamber 220.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein, but is limited only by the following claims.

What is claimed is:

1. A syringe device, wherein said syringe device comprises:
   a stem, wherein said stem comprises an axial chamber;
   a plunger; and
   a container, wherein said container comprises a chamber:
   wherein said plunger further comprises a cover and a tube, and wherein said tube allows fluid communication between said chamber and said axial chambers when said cover is open;
   wherein when said cover is closed, said cover prevents fluid communication between said chamber and said axial chamber; and
   wherein said plunger further comprises a protrusion, and wherein said cover is secured to said protrusion in said closed position via a soluble substance.

2. The syringe device of claim 1, wherein said stem further comprises a secondary channel, and wherein said secondary channel provides fluid communication between said chamber and said tube, and said axial chamber.

3. The syringe device of claim 1, wherein said protrusion is parabolic.

4. The syringe device of claim 1, wherein said cover is secured to said protrusion via said soluble substance positioned proximate a periphery of said cover.

5. The syringe device of claim 1, wherein said tube comprises said soluble substance.

6. The syringe device of claim 5, wherein said soluble substance is positioned within said tube, and prevents fluid communication between said chamber and said axial chamber.

7. The syringe device of claim 5, wherein when said soluble substance positioned within said tube dissolves, said tube allows fluid communication between said chamber and said axial chamber.

8. The syringe device of claim 1, wherein said plunger further comprises a cavity, and wherein said tube comprises a tube bottom in fluid communication with said cavity.

9. The syringe device of claim 8, wherein said stem further comprises a base, and wherein said base is disposed against said cavity, and prevents fluid communication between said chamber and said axial chamber.

10. A method of using a syringe device of claim 1, said method comprising the step of:
    injecting said syringe into a vial holding a suspension media, wherein said soluble substance prevents fluid communication between said chamber and said axial chamber.

11. The method of claim 10, said method further comprising the steps of:
    pushing said stem inward to create positive pressure inside the vial of the suspension media; and
    pulling said stem outward to draw the suspension media into the syringe, wherein said soluble substance begins dissolving.

12. The method of claim 11, said method further comprising the steps of:
    pushing said stem inward to inject the suspension media into a vial of a dried medication; and
    pulling said stem outward to draw the medication now in suspension into the syringe.

13. The method of claim 12, said method further comprising the steps of:
    pushing said stem inward to inject the medication into a patient; and
    dissolving said soluble substance, wherein said chamber and said axial chamber are in fluid communication if said stem is not being pushed inward.

14. A syringe, where said syringe comprises:
    a stem, wherein said stem comprises a depresser and an axial chamber;
    a plunger; and
    a container, wherein said container comprises a chamber;
    wherein said plunger further comprises a conical shaped tube, and wherein said conical shaped tube allows fluid communication between said chamber and said axial chamber; and
    wherein said conical shaped tube further comprises a soluble substance, wherein said soluble substance prevents fluid communication between said chamber and said axial chamber.

15. The syringe of claim 14, wherein said stem further comprises a secondary channel, and wherein said secondary channel provides fluid communication between said chamber and said conical shaped tube, and said axial chamber.

16. The syringe of claim 14, wherein said soluble substance positioned within said conical shaped tube dissolves, said conical shaped tube allows fluid communication between said chamber and said axial chamber.

17. The syringe of claim 16, wherein said stem further comprises a base, and wherein said base comprises a base top, said plunger further comprises a cavity in fluid communication with said conical shaped tube having a tube bottom, and said base is disposed within said cavity; and wherein said base top is disposed proximate said tube bottom when said stem is being pushed inward to prevent fluid communication between said chamber and said axial chamber.

18. The syringe of claim 14, wherein said plunger further comprises a protrusion having a cover, and wherein said cover is secured to said protrusion via said soluble substance to prevent fluid communication between said chamber and said axial chamber via said conical shaped tube.

19. The syringe of claim 18, wherein said soluble substance positioned therein dissolves and releases said cover, said conical shaped tube allows fluid communication between said chamber and said axial chamber.

20. A syringe device, wherein said syringe device comprises:
 a stem, wherein said stem comprises an axial chamber;
 a container, wherein said container comprises a chamber, and wherein said soluble substance prevents fluid communication between said chamber and said axial chamber;
 a plunger, wherein said plunger further comprises a cover and a tube, and wherein said tube allows fluid communication between said chamber and said axial chamber when said cover is open, and wherein said plunger further comprises a protrusion, and wherein said cover is secured to said protrusion via said soluble substance.

21. The syringe device of claim 14, wherein said stem further comprises a secondary channel, and wherein said secondary channel provides fluid communication between said chamber and said axial chambers.

22. The syringe device of claim 21, wherein said plunger further comprises a cavity, and wherein said conical shaped tube comprises a tube bottom, and wherein said tube bottom is in fluid communication with said cavity.

23. The syringe device of claim 22, wherein said stem further comprises a base, and wherein said base is disposed against said cavity, prevents fluid communication between said chamber and said axial chamber.

24. The syringe device of claim 20, wherein said cover prevents fluid communication between said chamber and said axial chamber when said cover is closed.

25. The syringe device of claim 21, wherein said plunger further comprises a cavity, and wherein said tube comprises a tube bottom, and wherein said tube bottom is disposed at said cavity.

26. The syringe device of claim 25, wherein said stem comprises a base, and wherein said base is disposed against said cavity.

\* \* \* \* \*